DIAPER WITH HYDROPHOBIC YARNS

Original Filed Jan. 18, 1963

INVENTOR.
W. T. HOLLIDAY,
T. R. LYNCH &
W. H. FOOSHE, JR.
BY Warley L. Parrott
ATTORNEY

DIAPER WITH HYDROPHOBIC YARNS

Original Filed Jan. 18, 1963

INVENTORS
W. T. HOLLIDAY,
T. R. LYNCH &
W. K. FOOSHE, JR.
BY Warley L. Parrott
ATTORNEY

DIAPER WITH HYDROPHOBIC YARNS

Original Filed Jan. 18, 1963

INVENTORS
W. T. HOLLIDAY,
T. R. LYNCH &
W. K. FOOSHE, JR.
BY
Warley L. Parrott
ATTORNEY United States Patent Office Re. 26,515
Reissued Jan. 14, 1969

26,515

DIAPER WITH HYDROPHOBIC YARNS

Walter T. Holliday, Gaffney, Thomas R. Lynch, Ware Shoals, and Wesley K. Fooshe, Jr., Greenwood, S.C., assignors to Riegel Textile Corporation, a corporation of Delaware Original No. 3,113,570, dated Dec. 10, 1963, Ser. No. 252,505, Jan. 18, 1963. Application for reissue Feb. 27, 1964, Ser. No. 354,492
U.S. Cl. 128—284 6 Claims
Int. Cl. A61f *13/00;* A61l *15/00*

Matter enclosed in heavy brackets [ ] appears in the original patent but forms no part of this reissue specification; matter printed in italics indicates the additions made by reissue.

This invention relates to diapers and more particularly to a new diaper that has different moisture absorption characteristics on the two sides thereof. This diaper functions to draw moisture away from the baby's skin toward the absorbent outside of the diaper and thereby tends to keep the baby's skin dry.

An important feature of the diaper of this invention is the use of hydrophobic or non-water absorbing fibers predominately on one side of the diaper, that is, the side which will be placed in contact with the baby's skin, and hydrophilic or water absorbing fibers predominately on the opposite side. This construction is obtained by utilizing a suitable weave pattern in which hydrophobic fibers, e.g. synthetic fibers, *such as cellulose triacetate, polyamide, polyvinyl chloride, polypropylene, acrylic, modacrylic, and polyester fibers,* are utilized as warp yarns, and are caused to lie mainly on one face of the diaper fabric, and hydrophilic fibers, e.g. cotton or rayon, are used for the filling.

Examples of suitable weave patterns for bringing the hydrophobic fibers predominately to one surface are birdseye, sateen, sheen and twill weaves. In these weaves, the warp yarns "float" over filling yarns without intersecting at each crossing and where these warp yarns are composed of hydrophobic fibers, one face of the diaper fabric will be relatively non-water absorbent and the other face, which will consist predominately of the hydrophilic filling, e.g. cotton yarns, will be highly water absorbent. When this type diaper is placed with the hydrophobic warp yarn surface in contact with a baby, it will tend to draw the moisture away from the baby's skin and toward the outer water absorbent side of the diaper, thus minimizing the amount of moisture that will remain in contact with the baby's skin.

Heretofore, when it was desired to accomplish the above described function of the diaper of the present invention, a separate diaper liner was produced from hydrophobic fibers, such as for example polyvinyl chloride fibers as disclosed in the Charles Devaud Patent No. 2,894,511, issued July 14, 1959, or nylon fibers disclosed in the Harold F. Davidson Patent No. 2,905,176, issued September 22, 1959. These prior art constructions require the production and handling of a separate fabric which is placed so as to form a liner for the regular cotton diaper. In accordance with the present invention, the expense and other disadvantages connected with manufacturing and handling a separate liner material are avoided and a single unitary diaper is produced which accomplishes the desired moisture drawing action above described.

The diaper fabric of the present invention utilizing hydrophobic fiber warp yarns and hydrophilic filling yarns, may be incorporated in a diaper in a number of different forms, illustrative but non-limiting examples of which are as follows:

(a) A diaper may be fabricated by sewing in a panel of the hydrophobic face fabric in a position so as to allow the hydrophobic surface to be in contact with the baby's skin. This diaper may be adapted for folding by the user to accommodate different size babies or it may be prefolded and sewn by the fabricator.

(b) A single layer diaper with a center panel in a birdseye or similar weave consisting of hydrophobic warp yarns and hydrophilic filling yarns and with side panels consisting of hydrophilic warp and filling yarns, may be woven with the panels integral. The woven diaper with the center panel having a face consisting predominantly of hydrophobic warp yarns may be prefolded and sewn to provide a multi-layer diaper with hydrophobic fibers predominantly on the face of the top layer, or the diaper may be folded by the mother to accommodate it to the size of the baby and to dispose the predominantly hydrophobic face next to the baby for maximum moisture transfer action.

(c) A multiple layer diaper having one layer woven in a suitable weave pattern to dispose the hydrophobic fiber warp yarns thereof predominately on one side in the center or near center portion of that layer of fabric which is to be placed next to the baby, and a separate layer or layers woven with water absorbing hydrophilic yarns in any desired pattern, including a plain weave or birdseye weave, and these two or more layers being joined together at the coextensive edges thereof to produce a substantially unitary product possessing a drawing property in the first mentioned layer and a highly absorbent property in the other layer or layers. This multiple layer diaper may be fabricated into diapers of the prefolded and sewn type.

The diaper of the present invention will be further understood by reference to the following more detailed description taken in conjunction with the accompanying drawings in which.

Figure 1:
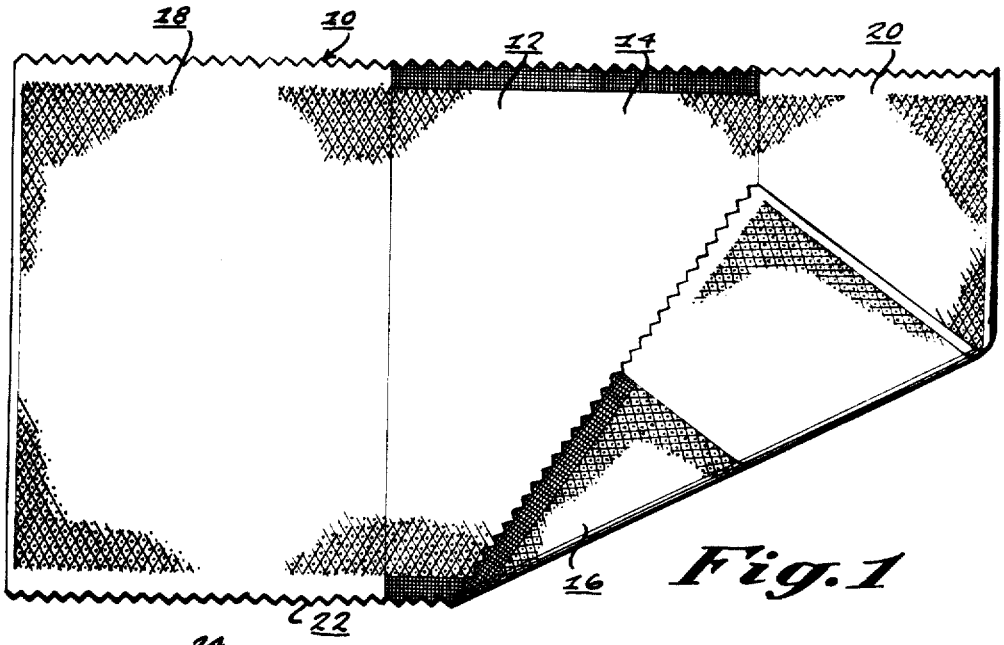
FIG. 1 is a plan view of a single ply unfolded diaper using a birdseye weave throughout with hydrophobic fibers in the warp of the center panel and hydrophilic fibers in both the warp and the filling of the two outer panels, and with one end turned up to show the reverse side.
Figure 2:
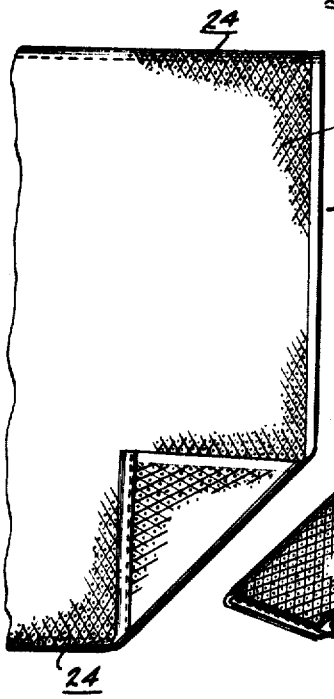
FIG. 2 is a fragmentary plan view showing one of the end panels of the diaper of FIG. 1 and with the cut edges of the diaper hemmed instead of pinked as shown in FIG. 1.

In FIG. 1, a diaper 10 using birdseye weave throughout is shown with center panel 12 woven with hydrophobic fibers in the warp, with one side 14 consisting predominately of said warp yarns, and the other side 16 consisting predominately of hydrophilic filling yarn, and two outer panels 18 and 20 woven with hydrophilic fibers as both warp and filling yarn. This single ply diaper 10 is folded in such a manner as to cause the side 14 of center panel 12 to be placed in contact with the skin when worn by a baby, thereby causing the moisture to be drawn away from the skin toward water absorbent side 16 of center panel 12, and into absorbent outer panels 18 and 20. The cut edges of the diaper 10 may be pinked as are edges 22 in FIG. 1, or hemmed as are the edges 24 of end panel 18 shown in FIG. 2.

Figure 3:
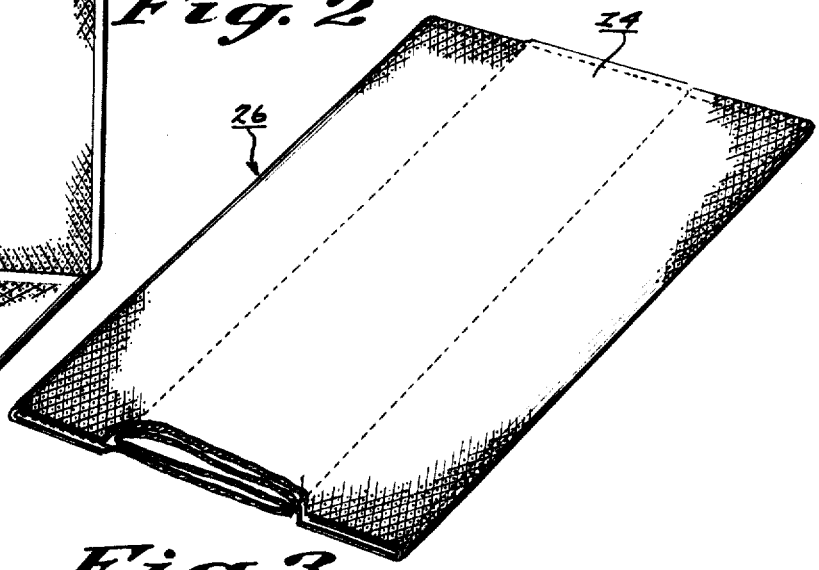
FIG. 3 is an elevational view of the single ply diaper shown in FIG. 1 with the cut edges hemmed as shown in FIG. 2, but folded and sewn to produce a prefolded diaper ready for use.

The single ply diaper 10 may be prefolded and sewn to produce a prefolded diaper 26 as shown in FIG. 3, with hydrophobic warp yarn surface 14 of center panel 12 being placed in contact with the skin when the diaper is placed upon a baby.

Figure 4:
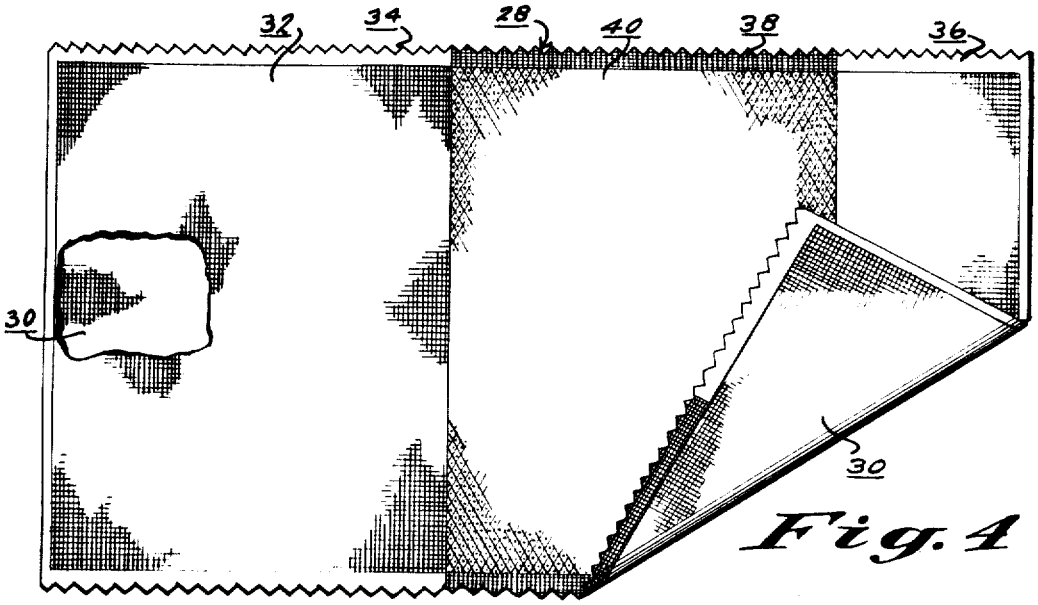
FIG. 4 is a plan view of an unfolded two ply diaper having in the top ply a hydrophobic fiber face center panel in a birdseye weave, with two outer plain weave all-hydrophilic fiber panels, with one end turned up to show the reverse side of the second ply and a portion broken away in one panel to indicate the other side of the second ply on the reverse side.

A second embodiment of the invention is shown in FIG. 4, wherein a diaper 28 comprised of two plies is illustrated. Ply 30, as shown in the turned up corner and cutaway portion of FIG. 4 is a single plain weave woven with hydrophilic yarns throughout. Ply 32 comprises plain weave hydrophilic outer panels 34 and 36, and birdseye weave center panel 38, which utilizes hydrophobic fibers as warp yarns and hydrophilic fibers as filling yarns, with the hydrophobic warp yarns predominating on the face 40. When worn, the diaper is folded and placed upon a baby with the face 40 in contact with the skin.

Figure 5:
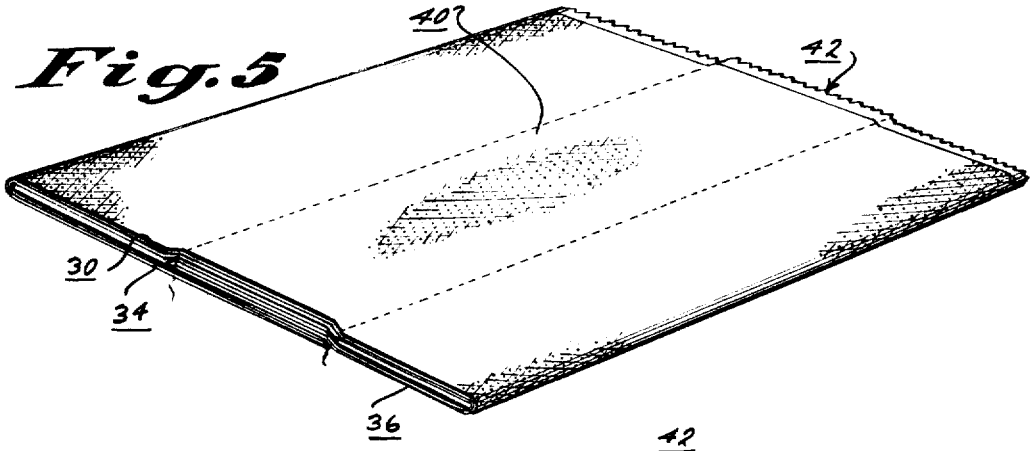
FIG. 5 is an elevational view of a two ply diaper similar to that shown in FIG. 4, but folded and sewn to form a prefolded diaper ready for use with the birdseye weave hydrophobic fibers on the top side, with one end sectioned to show the two plies and the multiple layers.
Figure 6:
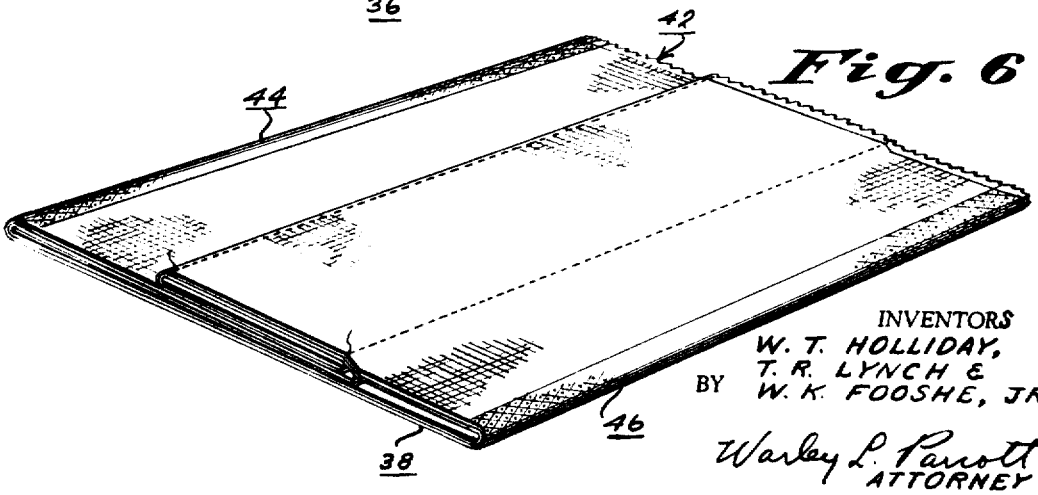
FIG. 6 is an elevational view of the reverse side of the diaper of FIG. 5, showing this reverse side covered by a plain weave ply except along the outer edges which are formed by extensions of the birdseye weave used on the front face.

The two ply diaper 28 may be folded and sewn to form a prefolded diaper 42 as shown in FIG. 5. The face 40, with warp yarns predominating, is placed in contact with the skin when the diaper is put upon a baby, with hydrophilic bottom ply 30 and hydrophilic panels 34 and 36 of top ply 32 comprising the outer layers of the diaper. Moisture is drawn through the non-absorbent fibers of face 40 and into the highly absorbent hydrophilic fibers of the outer layers, thus keeping the baby's skin dry and comfortable. The reverse side of the prefolded and sewn diaper 42 is shown in FIG. 6. The folded edges 44 and 46 are composed of the birdseye weave panel 38 to assure full contact of the hydrophobic portions of the diaper with the baby's skin.

Figure 7:
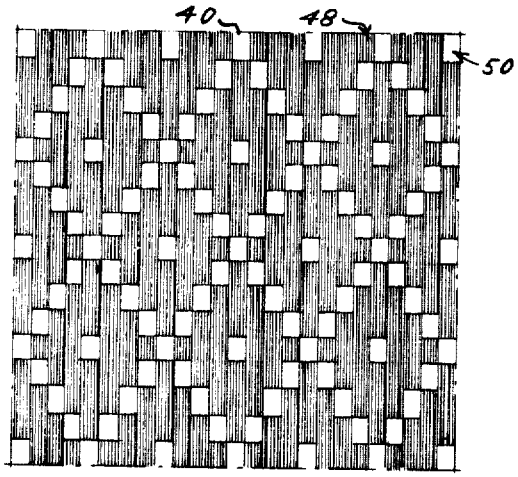
FIG. 7 is a diagrammatic illustration, greatly enlarged, of the face of a birdseye weave fabric consisting predominately of warp yarns.
Figure 8:
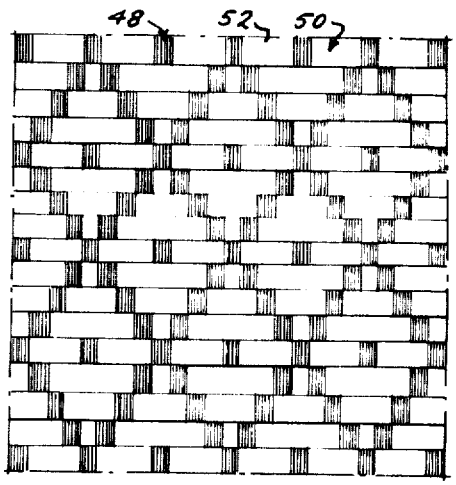
FIG. 8 is a diagrammatic illustration, greatly enlarged, of the back of a birdseye weave fabric and consisting predominately of filling yarns.

In FIG. 7 a portion of face 40 of a birdseye weave fabric consisting of hydrophobic warp yarns 48 and hydrophilic filling yarns 50 is shown, with the hydrophobic yarns predominating. FIG. 8 illustrates the reverse side 52 of a birdseye weave such as that shown in FIG. 7, with hydrophilic yarns 50 predominating over the hydrophobic yarns 48.

Figure 9:
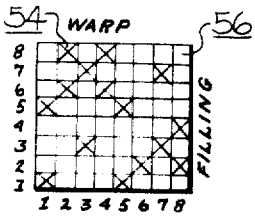
FIG. 9 is a diagrammatic illustration of the arrangement of the warp and filling yarns of the birdseye weave.
Figure 10:
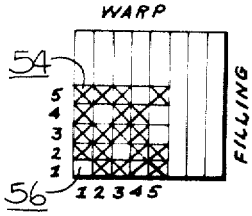
FIG. 10 is a diagrammatic illustration of the arrangement of the warp and filling yarns in a sateen weave.
Figure 11:
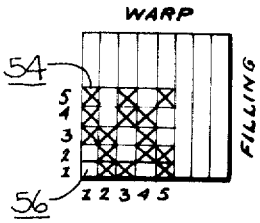
FIG. 11 is a diagrammatic illustration of the arrangement of the warp and filling in a sheen weave.

FIG. 9 illustrates a birdseye weave pattern, with warp yarns 54 running vertically and filling yarns 56 running horizontally. Examples of other weave patterns which may be used successfully in the diaper of the present invention are sateen, as illustrated by FIG. 10, and sheen, as illustrated by FIG. 11. In FIGS. 10 and 11, as in FIG. 9, warp yarns 54 run vertically and filling yarns 56 run horizontally.

Figure 12:
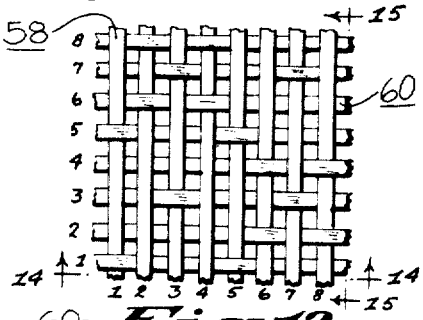
FIG. 12 is an enlarged schematic plan view of a portion of the hydrophobic fiber and hydrophilic fiber warp and filling yarns, respectively, in a birdseye weave.
Figure 13:
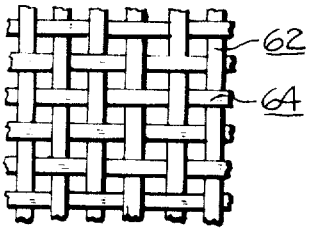
FIG. 13 is a fragmentary enlarged schematic plan view of the warp and filling yarns in a plain gauze weave.

FIG. 12 illustrates a birdseye weave with hydrophobic fiber warp yarns 58 and hydrophilic fiber filling yarns 60, with the warp yarns 58 predominating, as opposed to a plain gauze weave, shown in FIG. 13, in which warp yarns 62 and filling yarns 64 are equal.

Figure 14:
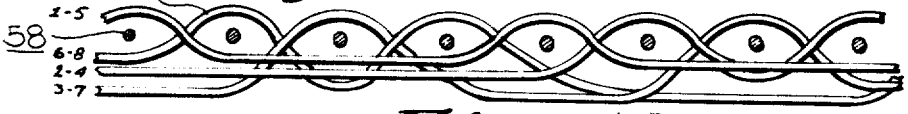
FIG. 14 is an enlarged sectional view taken along the lines 14—14 of FIG. 12.
Figure 15:
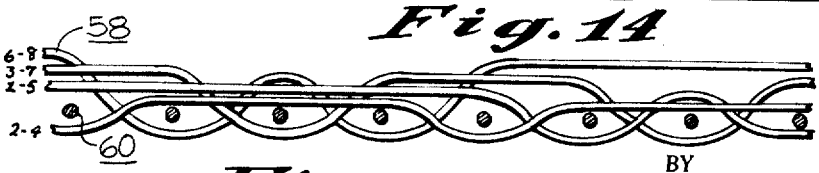
FIG. 15 is an enlarged sectional view taken along the lines 15—15 of FIG. 12.

FIGS. 14 and 15 are sectional views of the birdseye weave fabric shown in FIG. 12 and composed of hydrophobic fibers as warp yarns 58 and hydrophilic fibers as filling yarns 60.

The present invention has been described in detail above for purposes of illustration only and is not intended to be limited by this description or otherwise except as defined in the appended claims.

We claim:

1. A woven diaper adapted to be folded to form a front portion, rear portion, crotch portion, and leg apertures when placed in position on the wearer, said diaper comprising a single layer having hydrophobic yarns and hydrophilic yarns woven together, the hydrophobic yarns being predominantly on one side and the hydrophilic yarns being predominantly on the other side and adapted when folded and worn to have the side containing predominantly hydrophobic yarns in contact with the skin of the wearer to draw moisture away from the skin and the other side of said layer containing predominantly hydrophilic yarns being adapted to hold the moisture away from the skin of the wearer.

2. A woven diaper as set forth in claim 1, in which, the hydrophobic yarns comprise polypropylene.

3. A woven diaper as set forth in claim 1, in which, said single layer comprising hydrophobic yarns and hydrophilic yarns constitutes a central panel of the diaper, and at least one panel on each side of said center panel woven entirely of said hydrophilic yarns.

4. A woven diaper as set forth in claim 1, in which, said diaper comprises at least two layers of woven textile material, one of said layers having at least a center portion woven from said hydrophobic yarns and said hydrophilic yarns, and the other of said layers being woven entirely of hydrophilic yarns and adapted to hold moisture away from the skin of the wearer.

5. A woven diaper adapted to be folded to form a front portion, rear portion, crotch portion, and leg apertures when placed in position on the wearer, said diaper comprising two layers of woven textile material, one of said layers having at least a center portion comprising hydrophobic yarns and hydrophilic yarns woven together, the hydrophobic yarns being predominantly on one side and the hydrophilic yarns being predominantly on the other side and adapted when folded and worn to have the side containing predominantly hydrophobic yarns in contact with the skin of the wearer to draw moisture away from the skin and the other side containing predominantly hydrophilic yarns being adapted to hold the moisture away from the skin of the wearer, the other of said layers being woven entirely of hydrophilic yarns and adapted to hold moisture away from the skin of the wearer, and said two layers of woven textile material being interwoven at each of the selvage edges to provide a unitary diaper.

6. A woven diaper as set forth in claim 5, in which, the portion woven from hydrophobic yarns and hydrophilic yarns utilizes the hydrophobic yarns as the warp yarns and the hydrophilic yarns as the filling yarns.

References Cited

The following references, cited by the Examiner, are of record in the patented file of this patent or the original patent.

UNITED STATES PATENTS

| | | | |
|---|---|---|---|
| 2,542,297 | 2/1951 | Sunbury et al. | 139—420 |
| 2,845,069 | 7/1958 | Jamison et al. | 128—284 |
| 2,894,511 | 7/1959 | Devaud | 128—284 X |
| 2,905,176 | 9/1959 | Davidson | 128—284 |

FOREIGN PATENTS

| | | |
|---|---|---|
| 1,165,801 | 6/1958 | France. |

CHARLES F. ROSENBAUM, *Primary Examiner.*

U.S. Cl. X.R.

139—420